United States Patent
Nagasaki et al.

(10) Patent No.: US 7,732,158 B2
(45) Date of Patent: Jun. 8, 2010

(54) METHOD OF HIGH-SPEED DETECTION FOR BIOLOGICAL ANALYTE

(75) Inventors: Yukio Nagasaki, Moriya (JP); Kazunori Kataoka, Tokyo (JP); Takehiko Ishii, Washimiya-machi (JP); Tadahito Takahashi, Yokohama (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 582 days.

(21) Appl. No.: 10/575,551

(22) PCT Filed: Sep. 6, 2004

(86) PCT No.: PCT/JP2004/013258

§ 371 (c)(1),
(2), (4) Date: Apr. 10, 2006

(87) PCT Pub. No.: WO2005/036172

PCT Pub. Date: Apr. 21, 2005

(65) Prior Publication Data

US 2007/0059843 A1    Mar. 15, 2007

(30) Foreign Application Priority Data

Oct. 10, 2003    (JP) .............................. 2003-352669

(51) Int. Cl.
  *G01N 33/53*    (2006.01)
  *G01N 33/553*   (2006.01)
  *G01N 33/544*   (2006.01)
  *G01N 33/547*   (2006.01)
  *G01N 33/537*   (2006.01)

(52) U.S. Cl. ...................... 435/7.92; 436/525; 436/528; 436/532; 436/539

(58) Field of Classification Search ................ 436/523, 436/525, 528, 532, 539; 435/7.92; 530/402, 530/403
See application file for complete search history.

(56) References Cited

U.S. PATENT DOCUMENTS

| 4,362,531 A | * | 12/1982 | De Steenwinkel et al. .. 436/512 |
| 5,750,411 A | * | 5/1998 | Sommer ...................... 436/525 |
| 5,981,296 A | * | 11/1999 | Stout ........................... 436/501 |
| 2003/0013133 A1 | | 1/2003 | Kataoka et al. |

FOREIGN PATENT DOCUMENTS

| JP | 7-83928 | 3/1995 |
| JP | 2001-146556 | 5/2001 |
| JP | 2001-208754 | 8/2001 |
| JP | 2001-324507 | 11/2001 |
| WO | 02/097436 | 12/2002 |

* cited by examiner

*Primary Examiner*—Shafiqul Haq
(74) *Attorney, Agent, or Firm*—Wenderoth, Lind & Ponack, L.L.P.

(57) ABSTRACT

This invention provides a method to detect analyte which comprises preparing fine particles which have a chargeable group in their core and a hydrophilic polymer chain in their shell; obtaining an agglutinated matter by forming a biologically specific bond between a specific residue on the surface of fine particles and analyte, and by simultaneously forming a bond by the electrostatic interaction between impure protein and said particles; and subsequently cleaving only the latter bond by raising ionic intensity. Thus, this invention provides a method to detect analyte with rapidity and high sensitivity with use of agglutination reaction.

10 Claims, 2 Drawing Sheets

(a)

(b)

METHOD OF HIGH-SPEED DETECTION FOR BIOLOGICAL ANALYTE

Related Applications

This is a US national phase filing under 35 U.S.C. §371 of PCT/JP04/13258 filed Sep. 6, 2004 and claims priority from JP 2003-352669 filed Oct. 10, 2003.

TECHNICAL FIELD

This invention relates to a method for biologically detecting analyte, more specifically to a method for detecting analyte with use of agglutination reaction.

BACKGROUND ART

In a method for detecting analyte which is well-known in this field, latex or erythrocyte is sensitized with antigen or antibody beforehand, and, then, agglutination reaction with an analyte which exists in biological fluid such as protein or a certain specific organic material is utilized for detecting the analyte. An example of latex which has widely been employed for the above-mentioned method is polystyrene latex, which is being studied also as to what influence is exerted on analyte-detecting rate or the sensitivity of detection (e.g., non-specific adsorption of materials other than analyte, or the like) by factors such as particle size and functional group (carboxyl group and the like) on the surface of particle (see Journal of the Japan Society for Clinical Laboratory Automation, 12, 2, 121-124, 1987).

Agglutination of latex particles via analyte has a major influence on detecting rate. It takes, however, a considerable time for the agglutination, since the speed of said agglutination is determined by diffusion. Hence, it has been tried, for instance, to make latex particles carry magnetic particles and to raise the rate of agglutination or precipitation of latex particles by magnetic force (see, e.g., J. Applied Polymer Science, Vol. 50, 765-776, 1993).

Polystyrene latex particles and the like which are mentioned in the former of the above-mentioned documents are liable to agglutinate non-specifically, and are sometimes slightly inferior in dispersion stability. Furthermore, the surface of such particles is apt to non-specifically adsorb impure protein other than analyte. Thus, a part of the inventors of this invention has provided, as a quantum dot to detect analyte in biological sample, composite particles which are composed, for instance, of semiconductor-ultra fine particles-encapsulating fine particles whose surface is covered with chain of polyethylene glycol (hereinafter referred to also as PEG) or poly(ethylene oxide) (or wherein PEG having high mobility in an aqueous solution takes plural brush-like structures) (see pamphlet of WO 02/056020, pages 16-17). Although this type of quantum dot prevents non-specific adsorption of impure protein, it has generally a particle size up to hundreds of nanometers, and has high-mobility PEG on its surface. Thus, quantum dot makes a very stable dispersion in an aqueous solution, and has therefore not necessarily been considered to be suitable for use in a system to rapidly detect analyte with use of agglutination reaction.

DISCLOSURE OF INVENTION

The objective of this invention is to provide a method to rapidly detect analyte, which prevents non-specific adsorption of impure protein in a biological sample, and which uses no magnetic force or the like.

The inventors of this invention have found out that, when such fine particles as mentioned in pamphlet of WO 02/056020 whose surface is covered with chain of high-mobility PEG or other hydrophilic polymer have a chargeable group in an aqueous solution which contains proteins or the like, and when said group is in a charged state, said fine particles instantly agglutinate by electrostatic interaction with a certain protein.

The inventors have further found out the following fact. In an aqueous solution which contains avidin as an analyte together with other protein, when said fine particles carry on their surface a companion (e.g., a residue of biotin derivative) to form a biologically specific bond, avidin which is the other companion also takes part in the instant agglutination of fine particles together with the above-mentioned certain protein. When thus agglutinated matter is put under a condition (e.g., raised ionic intensity) which cleaves the bond made by electrostatic interaction but does not cleave the above-mentioned biologically specific bond, only said biologically specific bond can actually be selectively retained (only the matters agglutinated via specific bond can be selectively retained). It has been confirmed that only a very short time is required for the whole process of the formation of agglutinated matter by the above-mentioned electrostatic interaction and biologically specific bond, and for subsequent selective deagglutination of only the matters which have been agglutinated by electrostatic interaction.

This invention has been completed by the above-mentioned findings. Thus, this invention provides a method to detect analyte in an aqueous solution with use of agglutination reaction of polymer-based fine particles dispersed in said solution, which is characterized by:

(a) said fine particle has, as a core, a polymer chain segment with a chargeable group-carrying recurring unit, and has, either as plural brush-like structures on said core or as a shell, nonionic hydrophilic polymer chain or segment of said hydrophilic polymer chain, a residue of a member of a biologically specific bond which is a counterpart to analyte being bound to at least a part of free terminals of said hydrophilic polymer chain, (b) agglutination reaction is conducted under a condition under which fine particles whose chargeable group is in a charged state can agglutinate via analyte, and, subsequently, thus agglutinated matter is treated under a condition under which, although the biologically specific bond between fine particles is not cleaved, the bond made by electrostatic interaction can be cleaved, and (c) the existence of agglutinated matter which remains after the treatment of step (b) is used as an index of the presence of analyte.

The detection method of this invention makes it possible to rapidly detect analyte (protein or other targeting material) with high sensitivity and under hardly any influence from impure protein in biological sample.

BEST MODE FOR CARRYING OUT THE INVENTION

Figure 1:
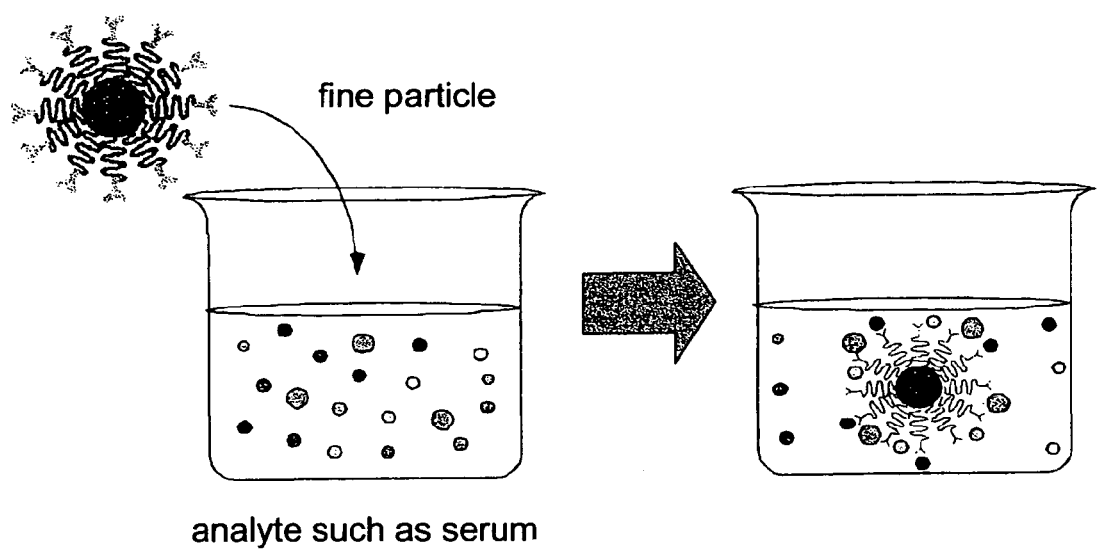
FIG. 1 is a conceptual figure of (a) the formation of bond by electrostatic interaction, and (b) the selective retention of biologically specific bond, both in accordance with this invention.
Figure 1:
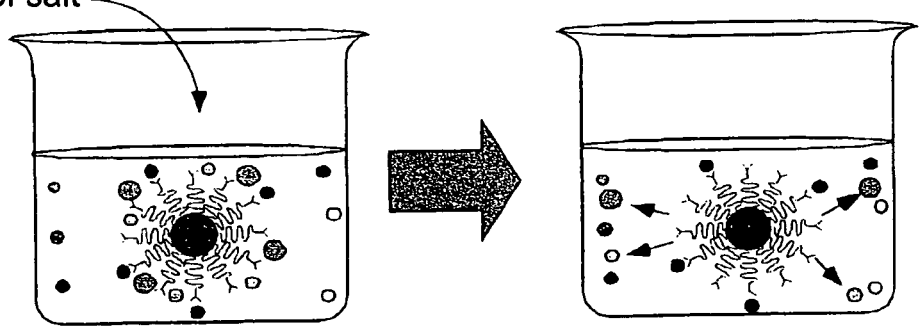

The method of this invention is capable of detecting any material as analyte so long as it is a compound or molecule which can take part in biologically specific bond. Examples of analyte include high-molecular material such as protein and polysaccharide, low-molecular targeting material which can be hapten (medicines, toxic materials, etc.), hormone, neuropeptide, and the like. Said compound includes natural products or modifications thereof, semi-synthesized compounds and chemically synthesized materials. As a sample which contains such a compound, there can be mentioned biological fluid such as blood, urine and saliva, a treating liquid which contains a diluted or concentrated solution of said biological fluid, and an aqueous solution which contains a reaction mixture from the biological or chemical conversion of targeting material.

In this invention, an aqueous solution which contains the above-mentioned biological fluid or chemically synthesized mixture is also called biological fluid or sample. Targeting material, hapten, antigen, antibody, sugar, lectin, hormone, neurotransmitter and receptor for targeting material or hormone are called biological analyte or simply analyte.

Thus, the above-mentioned biological sample can be mentioned as a typical example of aqueous solution in which agglutination reaction of polymer-based fine particles occurs. In accordance with this invention, even hapten, antigen and low-molecular peptide hormone can be analyte in this invention so long as they have polyfunctionality with regard to their corresponding antibody, receptor protein or the like. Although this invention is not restricted by this theory, when impure protein which may exist in sample is bound to fine particles by electrostatic interaction, the above-mentioned analyte is also capable of transferring with said impure protein, and is capable of bonding to a residue of one of companion pieces of biologically specific bond which is carried on fine particles. Of course, when the analyte is a protein, it moves together with other impure proteins, and is capable of bonding to a residue of said one of companion pieces. Not restrictively, said one of companion pieces can be one companion of pairs like antigen or hapten and antibody; hormone or neurotransmitter and corresponding receptor; and substrate and enzyme. Said protein includes glycoprotein, lipoprotein or the like.

Polymer-based fine particle is, in other words, fine particle which mainly comprises polymer, and may contain inorganic ultrafine particle which will be mentioned later, and any other material which has no adverse effects on the stability of fine particles per se, and on the achievement of the objective of this invention. Such a fine particle contains a chargeable group-carrying recurring unit. Said chargeable group may exist either on polymer main chain or on polymer side chain. The term "chargeable" means that the group is charged under a certain condition in an aqueous solution, e.g., under a suitable pH. Concrete examples of chargeable group in this invention include tertiary amino group, secondary amino group, carboxyl group (—COOH), sulfo group (—SO$_3$H) and phosphono group

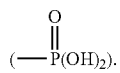

Chargeable group which can exist on polymer main chain are tertiary amino group and secondary amino group. As for the tertiary amino group and secondary amino group, two kinds of groups may exist on one and the same polymer chain segment. Also with regard to carboxyl group, sulfo group and phosphono group, two or more kinds of groups may exist on one and the same polymer chain segment.

Examples of polymer chain segment with a recurring unit carrying such a chargeable group as mentioned above include poly(alkylene amine) which has secondary amino group on polymer main chain. Examples of polymer which has amino group on side chain includes those whose polymer chain is either composed of monomer having a general formula (A):

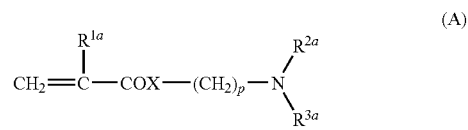

wherein $R^{1a}$ denotes a hydrogen atom or a $C_{1-6}$ alkyl group, $R^{2a}$ and $R^{3a}$ either, independently, denote a $C_{1-6}$ alkyl group or, taken together, may form, with the nitrogen atom to which they are bound, a five- or six-membered heterocycle which may contain further one or two nitrogen atoms, an oxygen atom or a sulfur atom, X denotes —O— or —NH—, and p denotes an integer of 2 to 6;

or composed of monomer having a general formula (B):

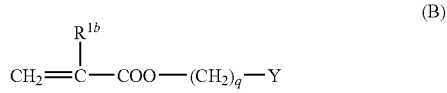

wherein $R^{1b}$ denotes a hydrogen atom or a $C_{1-6}$ alkyl group, Y denotes carboxyl group (—COOH), sulfo group (—SO$_3$H), oxysulfo group (—OSO$_3$H) or oxyphosphono group

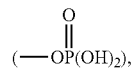

q denotes an integer of 0 to 4, provided that, when q is 0, Y denotes a hydrogen atom;

or composed of poly(amino acid derivative) selected from the group consisting of poly(lysine), poly(3-ω-N,N-di $C_{1-6}$ alkylamino-$C_{2-4}$ alkyl aspartate), poly(4-ω-N,N-di $C_{1-6}$ alkylamino-$C_{2-4}$ alkyl glutamate), poly(aspartic acid) and poly(glutamic acid).

In the above-mentioned formulae, substituents having the same definition have the same meaning unless otherwise specified. For instance, $C_{1-6}$ alkyl group is intended, in common, to mean a straight chain or branched chain alkyl having 1 to six carbon atoms, e.g., methyl, ethyl, n-propyl, iso-propyl, n-butyl, sec-butyl, tert-butyl, n-pentyl, n-hexyl, etc.

Examples of five- or six-membered heterocycle which $R^{2a}$ and $R^{2b}$, taken together, form with the nitrogen atom to which they are bound in formula (A) include the following:

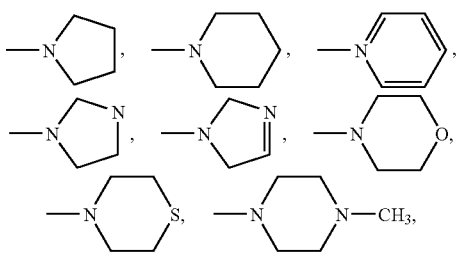

Examples of nonionic hydrophilic polymer chain in polymer-based fine particles, on the other hand, include those originated in polymer which is selected from the group consisting of polyethylene glycol, poly(vinyl alcohol), poly(vinyl pyrrolidone) and poly(N,N-dimethylacrylamide). Among those, polymer chain originated in polyethylene glycol is in particular desirable for the purpose of this invention. In the above, the phrase "originated in polymer" means that only small atom such as hydrogen or small molecule such as hydroxyl group is removed from one or both terminals of polymer.

Hydrophilic polymer chain or segment of said hydrophilic polymer chain, and a polymer chain with a chargeable group-carrying recurring unit or a segment of said polymer chain may be prepared by connecting two or three kinds of chains by any known connecting means, e.g., by dehydration condensation, polyaddition and spacer. In another method, firstly a polymer chain is previously prepared, and, thereafter, on one terminal of said polymer chain, the other chain is grown by polymerization from monomer, and, thus, there is given a block copolymer for the formation of fine particles to be used in this invention. A typical example of such a copolymer are, not respectively, those of the following formula (A-1) which is mentioned in Kataoka et al., Macromolecules 1999, 32, 6892-6894, as follows:

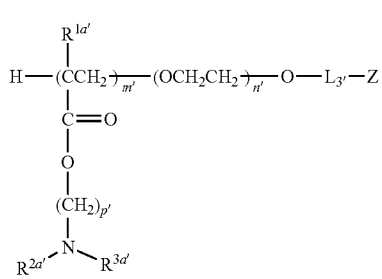

(A-1)

wherein
$R^{1a'}$ denotes a hydrogen atom or a $C_{1-6}$ alkyl group, $R^{2a'}$ and $R^{3a'}$ independently denote a $C_{1-6}$ alkyl group,
$L^{3'}$ denotes a $C_{1-6}$ alkylene or a valence bond,
Z denotes a hydrogen atom, a hydroxyl group, a carboxyl group, an amino group or an aldehyde group, provided that, when Z denotes a hydrogen atom, $L^{3'}$ denotes a valence bond,
m' denotes an integer of 1 to 10,000,
n' denotes an integer of 10 to 20,000, and
p' denotes an integer of 2 to 6.

Examples of block copolymer wherein hydrophilic polymer chain is originated in polyethylene glycol and wherein polymer chain with a chargeable group-carrying recurring unit is originated in poly(amino acid derivative) include the one which is mentioned in Japanese Patent 2690276 or a modification thereof.

In another method, a macro monomer corresponding to hydrophilic polymer chain segment is previously prepared, and, then, said macro monomer is copolymerized with a chargeable group-carrying monomer, if necessary together with a crosslinking agent and/or a diluting monomer which contains an ethylenically polymerizable group. Thus obtained random copolymer is also usable for the formation of fine particles of this invention. In the following explanation, fine particles which are usable in this invention are formed with use of, not restrictively, poly(ethylene glycol) macro monomer having formula (M):

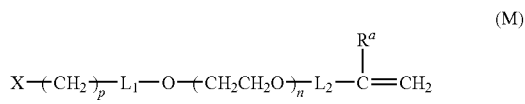

(M)

wherein X denotes a hydrogen atom, —COOM group (M denotes a hydrogen atom or an organic group), —$CHR^1R^2$ ($R^1$ and $R^2$ either independently denote a $C_{1-6}$ alkyloxy group, phenyloxy group or a phenyl-$C_{1-3}$ alkyloxy group, or, taken together, denote —OCHR'—$CH_2$O— wherein R' denotes a hydrogen atom or a $C_{1-6}$ alkyl group) or —CH=O,
$R^a$ denotes a hydrogen atom or a $C_{1-6}$ alkyl group,
$L_1$ denotes a methylene group or a carbonyl group,
$L_2$ denotes a carbonyl group, a $C_{1-3}$ alkylene group or a $C_{1-3}$ alkylphenylene group,
n denotes an integer of 2 to 10,000, and
p denotes an integer of 1 to 5.

Incidentally, the alkyl part of $C_{1-6}$ alkyloxy, phenyl-$C_{1-3}$ alkyloxy and of $C_{1-3}$ alkylphenylene would be understood from the above explanation or examples concerning $C_{1-6}$ alkyl. Examples of $C_{1-3}$ alkylene include —$CH_2$—, —$(CH_2)_2$—, —$(CH_2)_3$—, —$(CH_2)CH(CH_3)CH_2$—, etc.

Desired fine particles can be produced by subjecting macro monomer of formula (M) to suspension polymerization, which is known in this field, in an aqueous medium with a monomer of formula (A):

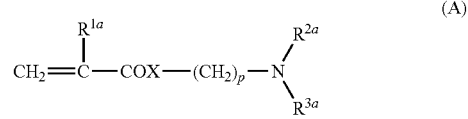

(A)

wherein $R^{1a}$ denotes a hydrogen atom or a $C_{1-6}$ alkyl group, $R^{2a}$ and $R^{3a}$ either, independently, denote a $C_{1-6}$ alkyl group or, taken together, may form, with the nitrogen atom to which they are bound, a five- or six-membered heterocycle which may contain further one or two nitrogen atoms, an oxygen atom or a sulfur atom, X denotes —O— or —NH—, and p denotes an integer of 2 to 6, and, if necessary, with a crosslinking agent of formula (C):

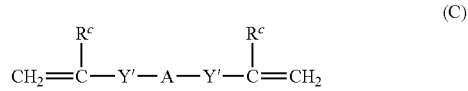

(C)

wherein $R^c$ denotes a hydrogen atom or a $C_{1-6}$ alkyl group, Y' denotes a valence bond, carbonyl group or —NH—, A denotes a phenylene group, —$(CH_2)_r$— (wherein r denotes an integer of 1 to 4) or —$(OCH_2CH_2O)_s$— (wherein s denotes an integer of 1 to 4), and further with, if necessary, a diluting monomer which contains ethylenically polymerizable group such as styrene, methyl(meth)acrylate, butyl(meth)acrylate, 2-ethylhexyl(meth)acrylate, (meth)acrylic amide, 2-hydroxyethyl methacrylate, isoprene, butadiene, etc.

A preferable embodiment is a crosslinked polymer which is produced with use of a crosslinking agent. For the production of such a crosslinked polymer, there are essentially used macro monomer of formula (M), monomer of formula (A) and crosslinking agent of formula (C) preferably in an amount of 10 to 70% by weight, 30 to 90% by weight and 0.1 to 20% by weight respectively, based on the total amount of (M), (A) and (C). More desirably, macro monomer of formula (M) is used in an amount of 10 to 50% by weight, monomer of formula (A) is used in an amount of 40 to 80% by weight, and crosslinking agent of formula (C) is used in an amount of 0.2 to 10% by weight. Particularly desirably, (M), (A) and (C) are used respectively in 15 to 30% by weight, 50 to 60% by weight and in 0.5 to 1% by weight. Diluting monomer may be used in an amount of 0.5 to 40 parts by weight per 100 parts by weight of total amount of the above-mentioned monomers.

Copolymerization reaction of the above-mentioned monomers is conducted under a condition under which a radical polymerization takes place, e.g., with using, as a solvent, water which may contain water-miscible organic solvent, methanol or ethanol, or preferably water alone, and, as an initiator, potassium persulfate, sodium persulfate, ammonium persulfate or 4,4'-azobis-4-cyanovaleric acid, if necessary under heating. A mixed solution of reacting materials may be subjected to reaction with vigorous stirring and with deaeration by inert gas (e.g., nitrogen, argon, etc.). Aliquot of reaction mixture is taken for analysis with, for instance, gas chromatography, and, thus, reaction is carried out until unreacted monomers disappear. In this manner, crosslinked polymer is generally obtained in the form of fine particles (or beads). Particle size of the fine particles can be adjusted in a range of from about 30 nm up to less than about 20 μm or even more, by choosing the proportion of (a) macromonomer, (b) comonomer and (c) crosslinking agent, and choosing the molecular weight of PEG of macromonomer (a). Thus, the fine particle of this invention can also be called microsphere. Generally, fine particle with a large particle size can be produced by increasing the proportion of comonomer in use. The size of mesh, on the other hand, can be adjusted by changing the proportion of crosslinking agent. When, as a diluting monomer, 2-hydroxyethyl methacrylate (HEMA) is used, the water-solubility of fine particles can be improved, and, when styrene is used, fine particles can be improved in refractive index.

Thus obtained fine particle (microsphere) can easily be produced with good reproducibility. A residue as a companion of a pair which forms a biologically specific bond can covalently be bound to this fine particle by any known condensation or addition method with use of the special property of PEG which mainly constitutes a shell domain or constitutes plural brushes from core, and with use of functional group which exists at a terminal.

Furthermore, the fine particle of crosslinked polymer of this invention can be provided as a finely particulate composite which has, encapsulated therein, an ultrafine particle of free electron metal such as gold, silver, copper, etc., or, not restrictively, of semiconductor as mentioned below, magnetic material or silica, by means of the mesh structure of the fine particle or by means of the part of tertiary amino group. It is well known that ultrafine particle of gold, silver, etc., has been utilized for labeling in biological assay system. It is also known that a nanocrystal of a kind of semiconductor such as, although not restrictive, ZnS, CdSe, CdS, InP, InAs, CdTe, ZnSe and ZnTe or a composite thereof is superior as a fluorescent label to organic dye (see, for instance, Chan et al., Science Vol. 281 (1998) 2016-2018; Mamedova et al., Nano Lett., Vol. 1 (2001) 282-286). Hence, the fine particle of this invention makes it possible to identify agglutinated matter which has been formed by an agglutination reaction, by means of energy transfer which occurs by interaction with adjacent particles.

"Ultrafine particle" in this invention means a particle of such a size as to be encapsulated in a fine particle of this invention. A semiconductor ultrafine particle, for instance, may have a particle size within a range of from 1 to 20 nm. Such a semiconductor ultrafine particle is capable of giving a fine particle having different wave lengths of emitted light, by the choice of the component of the semiconductor or by the choice of particle size.

Such a fine particle (also called microsphere) which has an ultrafine particle of metal or semiconductor encapsulated therein can be produced by mixing a microsphere of this invention with a sol of ultrafine particles of metal or semiconductor in an aqueous medium with stirring. Ultrafine particle of semiconductor can be encapsulated also by mixing an aqueous solution of chloride or the like of an element of group IIB or IIIB of periodic table with an aqueous solution of the above-mentioned fine particles with stirring by which to encapsulate said element in the fine particles, and then mixing the resultant solution either with an aqueous solution of an element of group VIB and a salt of alkali metal, or with $H_2S$, with stirring, by which to form in situ a semiconductor in a fine particle.

The production of fine particles from the aforementioned block copolymer can be conducted by any method that is well known in this field. Ultrafine particle of inorganic material can be encapsulated in said fine particle by just the same method as disclosed in the pamphlet of WO 02/056020 or by the slight modification thereof.

Thus produced fine particles based on polymer which may have ultrafine particle of various kind of inorganic materials encapsulated therein are stably dispersed in aqueous solution, and, then, the whole of each of particles may be slightly charged either positively or negatively, on account of chargeable group in the core. As shown in the conceptual drawing of FIG. 1(a), when such fine particles are added to a biological fluid (e.g., serum) which has been adjusted to a suitable pH value, said fine particles instantly bond or adsorb impure protein or the like (middle-sized gray-painted circle) which has a charge opposite to that of the fine particles, and bond or adsorb analyte (small-sized black-painted circle) which is to be specifically bound to a companion (indicated by Y-shaped symbol) of a pair which is to form a biologically specific bond on the surface of the fine particles (these bonds usually give rise to the formation of agglutinated matter between fine particles). When, subsequently, a salt is added to such a system, only specific bond can be maintained, as shown in the conceptual drawing of FIG. 1(b).

Condition for the bonding or adsorption of protein or analyte as shown in FIG. 1(a) may be changed according to the kind of chargeable group of fine particles used, or the kind of impure protein or the like. It would be desirable, therefore, that the skilled person should conduct beforehand a small-scale preparatory test to choose an optimal condition, before conducting a formal analyte-detecting test. When the chargeable group is a tertiary amino group, however, the above-mentioned bonding or adsorption can be caused by adjusting the pH of the biological fluid within a range of 6.5 to 10.0. Such bonding or adsorption takes place instantly. Then, also with regard to condition for retaining only the specific bond of analyte (i.e., condition under which, whereas biologically specific bond is not cleaved, the bond by electrostatic interaction is cleaved) from among the above-mentioned bonding or adsorption, it would be desirable to conduct a small-scale preparatory test to choose an optimal condition. When the chargeable group is a tertiary amino group, however, electrostatic interaction can be weakened, and the bond of impure protein can thereby be cleaved, by adjusting the concentration of salt (NaCl, Na$_2$CO$_3$, Na$_2$SO$_4$, etc.) to 0.1 to 2 M. Thus, impure protein can be eliminated from fine particles, and, so, only the bond of analyte can selectively be maintained. Since this elimination or deagglutination can be completed instantly, this invention makes it possible to detect analyte within seconds. The above-mentioned steps can be carried out either at room temperature, or from a low temperature at which biological fluid does not freeze to 80° C., according to the property of analyte.

Any method is usable for detection so long as it can distinguish between the state of FIG. 1(a) wherein bond or adsorption has taken place, and the state of FIG. 1(b) wherein selective elimination or deagglutination has taken place. Generally, the state of FIG. 1(a) can be distinguished from the state of FIG. 1(b) by the change of turbidity of fine particles, or, when the fine particle has a specific ultrafine particle of semiconductor encapsulated therein, by the change of fluorescent energy transfer (FRET) between the ultrafine particles. The amount of said change is in proportion to the amount of analyte in biological fluid, and, therefore, said change can be used as an index of the existence of analyte.

In the following, this invention is further explained by use of concrete examples, which are not intended to restrict this invention. Anyone skilled in the art would be able to understand any embodiment of this invention in the light of the aforementioned explanation and the following examples.

PRODUCTION EXAMPLE 1

Deblocking of Block Copolymer (PEG/PAMA=5000/14000), and Preparation of CdS-encapsulating Fine Particles with Use Thereof In this example, 22 ml of aqueous solution of acetic acid was added to 0.5 g of polymer (α-acetal-PEG-PAMA of the following formula obtained in accordance with the method as disclosed in the above-mentioned Kataoka et al., Macromolecules 1999, 32, 6892-6894; PEG Mw=5000 g/mol, PAMA (poly[(2-N,N-dimethylamino)ethylmethacrylate]) Mw=14, 000):

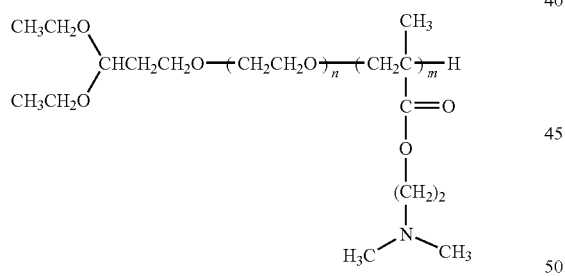

and the resultant mixture was stirred for five hours at 35° C., and, thus, terminal acetal group was converted to aldehyde (formyl). After the reaction was over, the mixture was neutralized with 37.4 ml of 10 M NaOH. Then, 1.0×10$^{-3}$ mol (0.038 g) of biotinhydrazide (manufactured by Pierce Co.) was added, and the resultant solution was stirred for two hours for reaction. The solution was subsequently reduced by the addition of 2.6×10$^{-4}$ mol of NaBH$_4$, and, then, the resultant solution was dialyzed against water for one day so that unreacted biotin and NaBH$_4$ might be removed (water was replaced three times). After dialysis was over, polymer was recovered by freeze drying. The polymer was measured by $^1$H-NMR, and, thus, it was confirmed that biotin had been introduced.

A vial was fed with 8 ml of ultra pure water and 2.465×10$^{-6}$ mol (0.048 g) of the above-prepared biotin-PEG-PAMA block copolymer, and the resultant mixture was dissolved by stirring for 30 minutes. Later, while the mixture was being stirred with a stirrer, a solution of CdCl$_2$ and a solution of Na$_2$S (each in an amount of 2.0×10$^{-5}$ mol) were added in order, and the resultant mixture was stirred for one hour. Thus obtained sample was kept in the dark, and, after one day, the sample was subjected to fluorescent spectrum measurement.

Thus obtained fine particles (also called biotinylated PEG-b-PAMA-CdS nanoparticles) were subjected to the measurement of surface zeta potential with LEZA-600 (manufactured by Otsuka Electronics Co., Ltd.). As a result, positive charge was shown at pH=7 or less (an aqueous solution of the fine particles was diluted so that the concentration might be 0.5 mg/ml).

PRODUCTION EXAMPLE 2

Preparation of Gel of Organic Nanoparticles

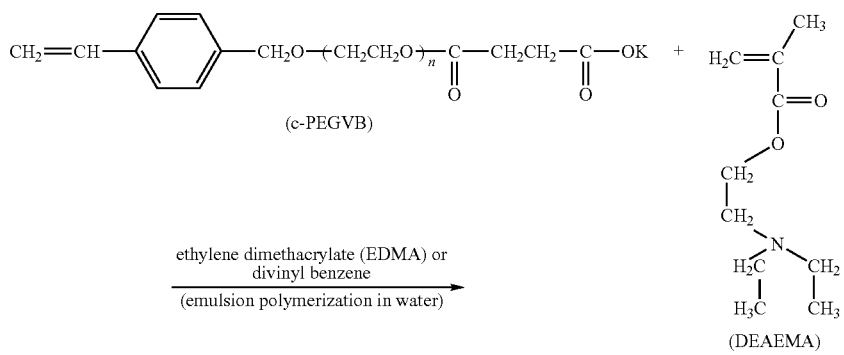

In the production of fine particles, the proportion by weight of polyethylene glycol macromonomer (c-PEGVB) to N,N-diethylaminoethyl methacrylate (DEAEMA) was changed from 1/0.5 to 1/100, and, thus, c-PEGVB-p (DEAEMA-EDMA) was prepared. As for the amount of each component, c-PEGVB and DEAEMA were used in 0.75 g in total, EDMA was added in a molar ratio of 1/(c-PEGVB+DEAEMA), potassium persulfate (KPS) was added in a molar ratio of 1/(c-PEGVB+DEAEMA+EDMA), and water was used in an amount of 15 ml. Production condition is shown in Table 1 as follows.

TABLE 1

Condition for the synthesis of c-PEGVB-p (DEAEMA-EDMA)

| Test No. | c-PEGVB/DEAEMA molar ratio | c-PEGVB/DEAEMA weight ratio | Amount added (mg) | | | |
|---|---|---|---|---|---|---|
| | | | c-PEGVB | DEAEMA | EDMA | KPS |
| 1 | 1/0.5 | 1/4.8 | 500 | 250 | 3.2 | 4.5 |
| 2 | 1/1 | 1/9.6 | 375 | 375 | 4.4 | 6.1 |
| 3 | 1/2 | 1/19 | 250 | 500 | 5.6 | 7.7 |
| 4 | 1/4 | 1/39 | 150 | 600 | 6.6 | 9.1 |
| 5 | 1/8 | 1/78 | 83 | 667 | 6.9 | 9.9 |
| 6 | 1/50 | 1/486 | 15 | 735 | 7.9 | 10.9 |
| 7 | 1/100 | 1/971 | 7 | 743 | 8.0 | 11.0 |

TABLE 2

Results of synthesis of c-PEGVB-p (DEAEMA-EDMA)

| Test No. | Average particle size (nm) | $\mu/\Gamma^2$ |
|---|---|---|
| 1 | 49.5 | 0.230 |
| 2 | 46.5 | 0.140 |
| 3 | 55.2 | 0.0940 |
| 4 | 62.9 | 0.0438 |
| 5 | 82.3 | 0.0881 |
| 6 | 196 | 0.0926 |
| 7 | 341 | 0.0206 |

PRODUCTION EXAMPLE 3

Production of c-PEGVB-p (DEAEMA-DVB)

In the production of nanosphere, the molecular weight of c-PEGVB was changed from 1800 to 7300, and, thus, c-PEGVB-p (DEAEMA-DVB) was prepared. As for the amount of each component, c-PEGVB and DEAEMA were used in 0.75 g in total, divinyl benzene (DVB) was added in a molar ratio of 1/(c-PEGVB+DEAEMA), KPS was added in a molar ratio of 1/(c-PEGVB+DEAEMA+DVB), and water was used in an amount of 15 ml. This production condition is shown in Table 3 below.

TABLE 3

Condition for the synthesis of c-PEGVB-p DEAEMA-EDMA)

| Test No. | PEG molecular weight | c-PEGVB/DEAEMA molar ratio | c-PEGVB/DEAEMA weight ratio | Amount added (mg) | | | |
|---|---|---|---|---|---|---|---|
| | | | | c-PEGVB | DEAEMA | DVB | KPS |
| 1 | 1800 | 1/4 | 1/39 | 150 | 600 | 4.3 | 9.1 |
| 2 | 4200 | 1/20 | 1/453 | 36 | 714 | 5.0 | 10.5 |
| 3 | 7300 | 1/10 | 1/394 | 68 | 682 | 4.8 | 10.1 |

Concretely, a reactor was fed with 0.15 g of c-PEGVB [α-vinylbenzyl-ω-carboxylpolyethylene glycol (number average molecular weight of polyethylene glycol macromonomer: 1800)], 9.1 mg of KPS and 15 ml of water, and the resultant mixture was stirred and dissolved. This reactor was then subjected to deaeration with aspirator. Furthermore, 6.6 μl of EDMA and 650 μl of DEAEMA were added to the aqueous solution of polyethylene glycol macromonomer/KPS with a syringe operation, and the resultant solution was stirred for 30 minutes at room temperature. Subsequently, the temperature was raised to 60° C., and the solution was stirred for 24 hours. After 24 hours, the reaction mixture was subjected to GC measurement, and, thus, it was confirmed that unreacted DEAEMA and EDMA had disappeared. Insoluble matters were filtrated out from thus produced polymer, and, so, an aqueous solution of fine particles (nanosphere) of c-PEGVB-p (DEAEMA-EDMA) was obtained.

Nanospheres prepared under certain synthetic conditions were measured for particle size and particle size distribution with DLS. Results are shown in Table 2 below.

Concretely, a reactor was fed with 0.15 g of c-PEGVB (number average molecular weight: 1800)], 9.1 mg of KPS and 15 ml of water, and the resultant mixture was stirred and dissolved. This reactor was then subjected to deaeration with aspirator. Furthermore, 4.8 μl of DVB and 6501 μl of DEAEMA were added to the aqueous solution of polyethylene glycol macromonomer/KPS with a syringe operation, and the resultant solution was stirred for 30 minutes at room temperature. Subsequently, the temperature was raised to 60° C., and the solution was stirred for 24 hours. After 24 hours, the reaction mixture was subjected to GC measurement, and, thus, it was confirmed that unreacted DEAEMA and DVB had disappeared. Insoluble matters were filtrated out from thus produced polymer, and, so, an aqueous solution of nanosphere of c-PEGVB-p (DEAEMA-DVB) was obtained.

The obtained nanospheres were evaluated in the same manner as in Example 3. Results are shown in Table 4 below.

TABLE 4

Results of synthesis of c-PEGVB-p (DEAEMA-EDMA)

| Test No. | Average particle size (nm) | $\mu/T^2$ |
|---|---|---|
| 1 | 65.0 | 0.064 |
| 2 | 52.0 | 0.078 |
| 3 | 56.0 | 0.093 |

Nanosphere of c-PEGVB-p (DEAEMA-DVB) which had been produced in accordance with Test Nos. 1, 2 and 3 of the above Production Example 3 were subjected to the measurement of zeta potential with LEZA-600 (manufactured by Otsuka Electronics Co., Ltd.). In more detail, each of aqueous solution of nanospheres was diluted to be 0.5 mg/ml, and, then, NaCl was added so that I=1.0×10$^{-2}$. By the addition of 1.0×10$^{-2}$ N—HCl or 1.0×10$^{-2}$ N—NaOH aqueous solution, pH was adjusted within a range of 2 to 10, and, thus, particles were measured for surface zeta potential. As a result, in each of test samples, positive charge was shown at pH=7 or more.

EXAMPLE 1

In this working example, Texas red-streptavidin (Tex SA) and Texas red-bovine serum albumin (BSA) were individually added to a solution which contained biotinylated PEG-b-PAMA-CdS which had been obtained in accordance with the above-mentioned Production Example 1. To thus prepared solutions, NaCl was added, and, then, subsequent energy transfer degree was observed. The concentration of each of samples was as follows:

| | CdS [(× 10$^{-5}$) mol/l] | Tex SA [(× 10$^{-5}$) mol/l] | NaCl (mol/l) |
|---|---|---|---|
| Sample of time 0 | 191 | 2.95 | 0 |
| Sample with the addition of NaCl | 191 | 2.95 | 0.15 |

Effects of Addition of NaCl on Energy Transfer Degree

Ultracentrifugation-purified solution of biotinylated PEG-b-PAMA-CdS nanoparticles was diluted to 1/8 concentration. From thus prepared solution, 0.5 ml was taken and put in each eppendorf tube. Tex SA and Texas Red BSA (which had previously been adjusted to have the same light emission intensity) were individually added, in an amount of 26 μl, to the solution in each eppendorf tube. After sufficient stirring with pipetting, 0.5 ml was dispensed for the measurement of fluorescent spectrum with use of a quartz microcell. Into the microcell, 0.005 ml of aqueous solution of NaCl (3.3 mol/l) was added, and, from immediately thereafter, fluorescent spectrum measurement was conducted with time (final concentration of CdS: 1.90×10$^{-3}$ mol/l; final concentration of Tex-SA: 2.9×10$^{-5}$ mol/l). Results are shown in FIG. 2.

Figure 2:
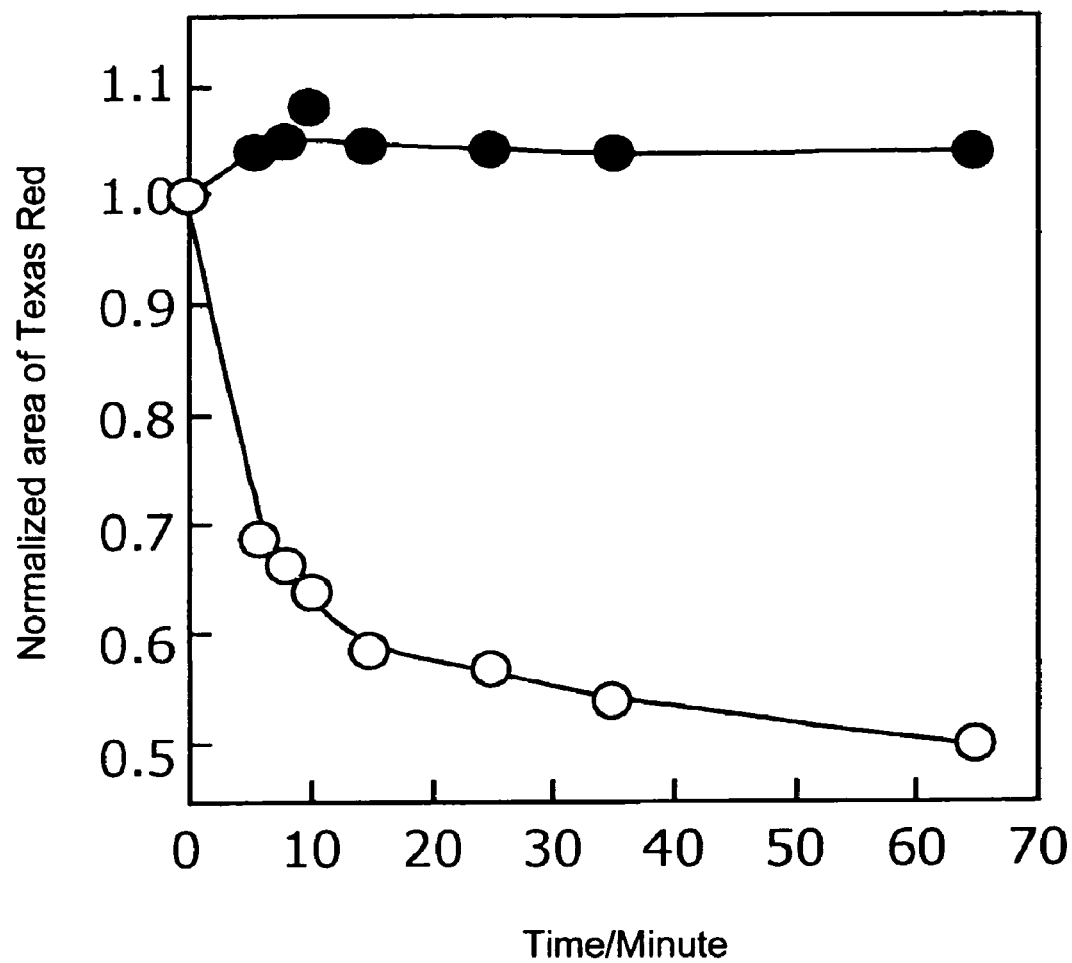
FIG. 2 is a graph which shows the effect of addition of NaCl on the degree of energy transfer of CdS-encapsulating fine particles in aqueous solution. ○ indicates the addition of Tex RSA 0.30 M NaCl, and ● indicates the addition of Tex SA 0.30 M NaCl.

It is seen in FIG. 2 that, when biotinylated PEG-b-PAMA-CdS nanoparticles are mixed with Tex SA or Texas-BSA at pH 7.4, light emission of 620 nm is instantly observed. After the addition of NaCl, volume increases by about 10%, and, accordingly, light emission intensity also decreases by about 10% in the system of Tex SA. In the system of Texas-BSA, on the other hand, the decrease of light emission was remarkable in comparison with SA. Light emission intensity more decreased as the ionic intensity increased, and, therefore, it is judged that non-specific adsorption via electrostatic interaction was inhibited by the neutralization of charge. Thus, by the above-mentioned operation, molecular recognition is quantified within a few seconds' mixing time.

INDUSTRIAL APPLICABILITY

By this invention, a molecular companion of a pair to form a biologically specific bond can be identified within a few seconds' mixing time by use of an agglutination reaction of fine particles. This invention is therefore usable for medical diagnosis and the like.

The invention claimed is:

1. A method to detect an analyte in an aqueous solution with use of an agglutination reaction of polymer-based fine particles dispersed in said solution, which comprises contacting the analyte with the polymer-based fine particle, wherein:
   (a) said fine particle has, as a core, a polymer chain segment with a chargeable group-carrying recurring unit, and has, as plural brushes on said core or as a shell, a hydrophilic polymer chain or segment of the hydrophilic polymer chain, wherein a member of a biologically specific bond which forms a counterpart to the analyte is bound to at least a part of free terminals of said hydrophilic polymer chain,
   (b) the agglutination reaction is conducted under a condition of a suitable pH under which the chargeable group is in a charged state and the fine particles can be bonded to the analyte or absorb the analyte to form agglutinated matter, and, subsequently, the agglutinated matter is treated under a condition of a raised ionic intensity, under which, although the biologically specific bond between the fine particles is not cleaved, a bond made by electrostatic interaction can be cleaved, and
   (c) the existence of agglutinated matter which remains after the treatment of step (b) is detected by a method capable of distinguishing a state in which the biologically specific bond is not cleaved, and a state in which the bond by electrostatic interaction is cleaved, the results being used as an index of the presence of analyte,
   wherein the hydrophilic polymer chain in the polymer-based fine particles is formed from a poly(ethylene glycol) macro monomer having formula (M):

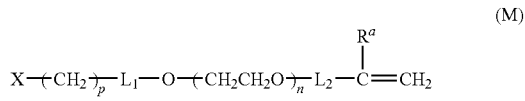

(M)

wherein
X denotes a hydrogen atom, —COOM group (M denotes a hydrogen atom or an organic group), —CHR$^1$R$^2$ (R$^1$ and R$^2$ either independently denote a C$_{1-6}$ alkyloxy group, phenyloxy group or a phenyl-C$_{1-3}$ alkyloxy group, or, taken together, denote —OCHR'—CH$_2$O— wherein R' denotes a hydrogen atom or a C$_{1-6}$ alkyl group) or —CH=O,
R$^a$ denotes a hydrogen atom or a C$_{1-6}$ alkyl group,
L$_1$ denotes a methylene group or a carbonyl group,
L$_2$ denotes a carbonyl group, a C$_{1-3}$ alkylene group or a C$_{1-3}$ alkylphenylene group,
n denotes an integer of 2 to 10,000, and
p denotes an integer of 1 to 5; and
wherein the polymer chain with a recurring unit carrying a chargeable group in the polymer-based fine particles is formed from a monomer having a formula (A):

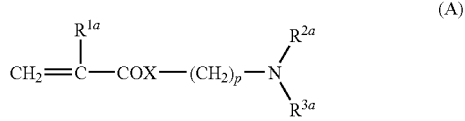

wherein $R^{1a}$ denotes a hydrogen atom or a $C_{1-6}$ alkyl group, $R^{2a}$ and $R^{3a}$ either, independently, denote a $C_{1-6}$ alkyl group or, taken together, may form, with the nitrogen atom to which they are bound, a five- or six-membered heterocycle which may contain further one or two nitrogen atoms, an oxygen atom or a sulfur atom, X denotes —O— or —NH—, and p denotes an integer of 2 to 6; and wherein said two monomers are copolymerized with a crosslinking agent and/or an ethylenically polymerizable group-containing diluting monomer to give a random copolymer, said crosslinking agent and diluting monomer being allowed, where necessary, to be mixed with each other before crosslinked.

2. The method of claim 1, wherein the chargeable group in the polymer-based fine particles is selected from the group consisting of tertiary amino group, secondary amino group, carboxyl group, sulfo group and phosphono group.

3. A method to detect an analyte in an aqueous solution with use of an agglutination reaction of polymer-based fine particles dispersed in said solution, which comprises contacting the analyte with the polymer-based fine particle, wherein:

(a) said fine particle has, as a core, a polymer chain segment with a chargeable group-carrying recurring unit, and has, as plural brushes on said core or as a shell, a hydrophilic polymer chain or segment of the hydrophilic polymer chain, wherein a member of a biologically specific bond which forms a counterpart to the analyte is bound to at least a part of free terminals of said hydrophilic polymer chain, wherein the polymer-based fine particles have, encapsulated in their core domain, an ultrafine particle of inorganic material which is selected from the group consisting of semiconductor, free electron metal, magnetic material and silica, (b) the agglutination reaction is conducted under a condition of a suitable pH under which the chargeable group is in a charged state and the fine particles can be bonded to the analyte or absorb the analyte to form agglutinated matter, and, subsequently, the agglutinated matter is treated under a condition of a raised ionic intensity, under which, although the biologically specific bond between the fine particles is not cleaved, a bond made by electrostatic interaction can be cleaved, and (c) the existence of agglutinated matter which remains after the treatment of step (b) is detected by a method capable of distinguishing a state in which the biologically specific bond is not cleaved, and a state in which the bond by electrostatic interaction is cleaved, the results being used as an index of the presence of analyte, wherein the hydrophilic polymer chain in the polymer-based fine particles is formed from a poly(ethylene glycol) macro monomer having formula (M):

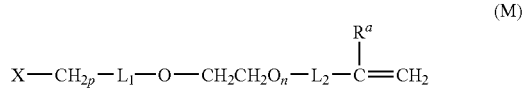

wherein
X denotes a hydrogen atom, —COOM group (M denotes a hydrogen atom or an organic group), —CHR$^1$R$^2$ (R$^1$ and R$^2$ either independently denote a $C_{1-6}$ alkyloxy group, phenyloxy group or a phenyl-$C_{1-3}$ alkyloxy group, or, taken together, denote —OCHR'—CH$_2$O— wherein R' denotes a hydrogen atom or a $C_{1-6}$ alkyl group) or —CH=O, $R^a$ denotes a hydrogen atom or a $C_{1-6}$ alkyl group,
$L_1$ denotes a methylene group or a carbonyl group,
$L_2$ denotes a carbonyl group, a $C_{1-3}$ alkylene group or a $C_{1-3}$ alkylphenylene group,
n denotes an integer of 2 to 10,000, and
p denotes an integer of 1 to 5; and wherein the polymer chain with a recurring unit carrying a chargeable group in the polymer-based fine particles is formed from a monomer having a formula (A):

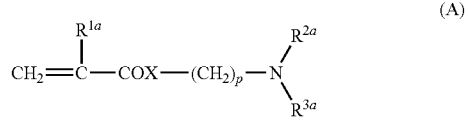

wherein $R^{1a}$ denotes a hydrogen atom or a $C_{1-6}$ alkyl group, $R^{2a}$ and $R^{3a}$ either, independently, denote a $C_{1-6}$ alkyl group or, taken together, may form, with the nitrogen atom to which they are bound, a five- or six-membered heterocycle which may contain further one or two nitrogen atoms, an oxygen atom or a sulfur atom, X denotes —O— or —NH—, and p denotes an integer of 2 to 6; and wherein said two monomers are copolymerized with a crosslinking agent and/or an ethylenically polymerizable group-containing diluting monomer to give a random copolymer, said crosslinking agent and diluting monomer being allowed, where necessary, to be mixed with each other before crosslinked.

4. The method of claim 3, wherein the polymer-based fine particles have, encapsulated in their core domain, an ultrafine particle of semiconductor.

5. The method of claim 1, wherein one of companion pieces of the biologically specific bond is one of antibody and its antigen or hapten; one of receptor protein and lectin, hormone and neurotransmitter which are to bond the receptor protein; one of streptavidin and biotin derivative; and one of enzyme and its substrate.

6. The method of claim 1, wherein the condition of a raised ionic intensity is putting the agglutinated matter under a high concentration of salt.

7. The method of claim 1, wherein the condition of a raised ionic intensity is adjusting the concentration of salt to 0.1 to 2 M.

8. The method of claim 3, wherein one of companion pieces of the biologically specific bond is one of antibody and its antigen or hapten; one of receptor protein and lectin, hormone and neurotransmitter which are to bond the receptor protein; one of streptavidin and biotin derivative; and one of enzyme and its substrate.

9. The method of claim 3, wherein the condition of a raised ionic intensity is putting the agglutinated matter under a high concentration of salt.

10. The method of claim 3, wherein the condition of a raised ionic intensity is adjusting the concentration of salt to 0.1 to 2 M.

* * * * *